United States Patent
Singh et al.

(10) Patent No.: US 7,115,281 B2
(45) Date of Patent: Oct. 3, 2006

(54) PROCESSES FOR THE PREPARATION OF ORAL DOSAGE FORMULATIONS OF MODAFINIL

(75) Inventors: Romi Barat Singh, Badshah Bagh (IN); Pannanchukunnath Manoj Kumar, Delhi (IN); Vishnubhotla Nagaprasad, Andhra Pradesh (IN); Sunilendu Bhushan Roy, Thane (IN); Rajiv Malik, Alaknanda (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 420 days.

(21) Appl. No.: 10/616,240

(22) Filed: Jul. 8, 2003

(65) Prior Publication Data

US 2004/0167225 A1    Aug. 26, 2004

(30) Foreign Application Priority Data

Jul. 8, 2002    (IN) .......................... 723/DEL/2002

(51) Int. Cl.
*A61K 9/16*    (2006.01)
*A61K 9/26*    (2006.01)
*A61K 9/48*    (2006.01)

(52) U.S. Cl. ...................... 424/489; 424/464; 424/465; 424/469; 424/470; 424/451; 424/452; 424/457

(58) Field of Classification Search ................ 424/489, 424/469–70, 457, 452, 465, 451, 464
See application file for complete search history.

(56) References Cited

U.S. PATENT DOCUMENTS

RE37,516 E    1/2002    Grebow et al. ............. 514/618

FOREIGN PATENT DOCUMENTS

GB    2293103    3/1996

*Primary Examiner*—Edward J. Webman
(74) *Attorney, Agent, or Firm*—Jayadeep R. Deshmukh, Esq.; William D. Hare, Esq.

(57) ABSTRACT

The invention relates to processes for preparing, and pharmaceutical compositions of, modafinil dosage forms for oral administration. The dosage forms include a mixture of coarse and fine particles of modafinil. The process for preparing modafinil oral dosage forms includes forming a dosage form that includes about 7%–25% by weight of modafinil particles having diameters greater than 220 μm and about 75%–93% by weight of modafinil particles having diameters less than 220 μm.

13 Claims, No Drawings

PROCESSES FOR THE PREPARATION OF ORAL DOSAGE FORMULATIONS OF MODAFINIL

FIELD OF THE INVENTION

The technical field of the invention relates to processes for preparing, and pharmaceutical compositions of, modafinil dosage forms for oral administration. The dosage forms include a mixture of coarse and fine particles of modafinil.

BACKGROUND OF THE INVENTION

Modafinil is a wakefulness-promoting agent indicated for use in narcolepsy and idiopathic hypersomnia. It also is used for improving memory and mood. Compared to amphetamines and methylphenidate, modafinil is less likely to cause jitteriness, anxiety, or excess locomotor activity. The precise mechanism of action is not fully understood but it is thought to modulate the central postsynaptic $alpha_1$-adrenergic receptors. However, modafinil has a different pharmacokinetic profile compared to the sympathomimetic agents, such as amphetamines and methylphenidate.

The benzhydrylsulfinyl acetamide structure of modafinil makes it insoluble in water (less than 1 mg/ml) as well as unstable at higher temperatures. These physicochemical properties decrease the drug's potential for abuse via injection or smoking, and lead to reduced cases of dependency compared to amphetamines.

Over the years, more than 40% of the potential candidates in drug discovery and research have failed to emerge as drugs due to their poor biopharmaceutic properties. Most of these are rejected due to poor solubility characteristics and further development is continued only if the new molecule has some marked advantage over the existing molecules indicated for the similar use.

The most common approach used to address the problem of insolubility is by either reducing the drug's particle size or micronizing the drug to the size of a few microns, which increases the effective exposed surface area. Dosage forms which contain micronized drug particles exhibit enhanced solubility and consequently an increase in the bioavailability of the drugs. However, technical and economical problems can arise. For example, highly micronized drug particles possess poor flow properties and an increased chance of re-agglomeration during processing. In some cases, re-agglomeration of micronized drug particles may be so problematic that the basic objective of enhancing the solubility by increasing the effective surface area may be unmet.

U.S. Pat. No. RE 37,516 discloses a method of size reduction and a pharmaceutical composition that has at least 95% of the modafinil particles having a diameter of less than 200 μm.

SUMMARY OF THE INVENTION

In one general aspect, there is provided a pharmaceutical composition of modafinil that includes a combination of coarse and fine particles of modafinil.

In another general aspect there is provided a process for preparing an oral dosage form containing modafinil. The process includes forming a dosage form that includes about 7%–25% by weight of modafinil particles have diameters greater than 220 μm and about 93%–75% by weight of modafinil particles have diameters less than 220 μm.

Embodiments of the process of forming the oral dosage form may include one or more of the following features. For example, forming a dosage form may further include mixing the modafinil particles in geometric progression with one or more pharmaceutically acceptable excipients to form a blend. Forming a dosage form may still further include granulating the blend to form granules, optionally drying the granules, sizing the granules, mixing the sized granules with one or more extragranular pharmaceutically acceptable excipients, and compressing into a tablet.

Forming the dosage form may further include blending the modafinil particles with one or more pharmaceutically inert excipients to form a blend, granulating the blend to form granules, blending the granules with one or more pharmaceutically inert excipients, and compressing or filling into a solid dosage form. Granulating may be wet granulation or dry granulation. The dosage form may be a tablet and the process may further include coating the tablet.

Forming the dosage form also may further include blending the modafinil particles with one or more pharmaceutically inert excipients to form a blend and compressing the blend or filling the blend into a solid dosage form.

Of the dosage form, about 7% by weight of the modafinil particles may have diameters greater than 220 μm and about 93% by weight of the modafinil particles may have diameters less than 220 μm. About 10% by weight of the modafinil particles may have diameters greater than 220 μm and about 90% by weight of the modafinil particles may have diameters less than 220 μm. About 15% by weight of the modafinil particles may have diameters greater than 220 μm and about 85% by weight of the modafinil particles may have diameters less than 220 μm. The specific surface area of the modafinil particles may be at least 0.2 $m^2/gm$. The dosage form may release at least 75% of the modafinil in about 45 minutes.

The oral dosage form may be a tablet or a capsule and the tablet is formed by either wet granulation, dry granulation, or direct compression. The process may further include coating the tablet.

The dosage form may include one or more pharmaceutically acceptable excipients. The pharmaceutically acceptable excipients may be one or more of binders, diluents, disintegrants, surfactants, lubricants, glidants, and coloring agents.

In another general aspect, there is provided an oral dosage form of modafinil including about 7% to 25% by weight of modafinil particles having diameters greater than 220 μm and about 93% to 75% by weight of modafinil particles having diameters less than 220 μm. The dosage form releases at least 75% of the modafinil in about 45 minutes.

Embodiments of the dosage form may include one or more of the following features. For example, about 7% by weight of the modafinil particles may have diameters greater than 220 μm and about 93% by weight of the modafinil particles may have diameters less than 220 μm. About 10% by weight of the modafinil particles may have diameters greater than 220 μm and about 90% by weight of the modafinil particles may have diameters less than 220 μm. About 15% by weight of the modafinil particles may have diameters greater than 220 μm and about 85% by weight of the modafinil particles may have diameters less than 220 μm. The specific surface area of the modafinil particles may be at least 0.2 $m^2/gm$.

The oral dosage form may be a tablet or capsule. The oral dosage form may further include one or more pharmaceutically acceptable excipients. The pharmaceutically acceptable excipients may be one or more of binders, diluents, disintegrants, surfactants, lubricants, glidants, and coloring agents.

In another general aspect, there is provided a method of treating a condition using modafinil. The method of treating includes providing an oral dosage form of modafinil that includes about 7% to 25% by weight of modafinil particles have diameters greater than 220 µm and about 93% to 75% by weight of modafinil particles have diameters less than 220 µm. The dosage form releases at least 75% of the modafinil in about 45 minutes.

Embodiments of the method of treating with modafinil may include one or more of the following features. For example, the condition may be one or both of narcolepsy and idiopathic hypersomnia.

Of the dosage form, about 7% by weight of the modafinil particles may have diameters greater than 220 µm and about 93% by weight of the modafinil particles may have diameters less than 220 µm. About 10% by weight of the modafinil particles may have diameters greater than 220 µm and about 90% by weight of the modafinil particles may have diameters less than 220 µm. About 15% by weight of the modafinil particles may have diameters greater than 220 µm and about 85% by weight of the modafinil particles may have diameters less than 220 µm. The specific surface area of the modafinil particles may be at least 0.2 $m^2/gm$.

The oral dosage form used to treat the condition may be a tablet or capsule. The oral dosage form may further include one or more pharmaceutically acceptable excipients. The pharmaceutically acceptable excipients may be one or more of binders, diluents, disintegrants, surfactants, lubricants, glidants, and coloring agents.

In another general aspect, there is provided an oral dosage form that includes an intragranular portion and an extragranular portion. The intragranular portion includes about 7% to 25% by weight of modafinil particles having diameters greater than 220 µm, about 93% to 75% by weight of modafinil particles having diameters less than 220 µm, and one or more pharmaceutically acceptable excipients. The extragranular portion includes one or more pharmaceutically acceptable excipients.

Embodiments of the oral dosage form may include one or more of the following features. For example, the oral dosage form may release one or more of between 48% and 81% of the modafinil within 15 minutes, between 68% and 87% of the modafinil within 30 minutes, between 76% and 95% of the modafinil within 45 minutes, between 84% and 97% of the modafinil within 60 minutes, and between 89% and 98% of the modafinil within 90 minutes. The modafinil is released in a USP Apparatus II, in 900 ml of water, and stirred at 50 rpm. The oral dosage form may be provided with labeling for one or more of wakefulness promotion, to improve wakefulness in patients with excessive daytime sleepiness associated with narcolepsy, and idiopathic hypersomnia.

The details of one or more embodiments of the inventions are set forth in the description below. Other features, objects, and advantages of the invention will apparent from the description and the claims.

DETAILED DESCRIPTION OF THE INVENTION

The inventors have recognized that there is an unmet need for a simple, cheaper, and faster process of preparing modafinil dosage forms having an improved dissolution rate without the processing problems of the prior art. In particular, the inventors have now discovered that the problem of reagglomeration of micronized modafinil particles can be avoided by mixing coarse particles (diameters greater than 220 µm) and fine particles (diameters less than 220 µm) in a ratio of between about 7:93 to about 25:75 by weight. The combination of coarse and fine particles of the drug improves the flow properties of the composition and thereby facilitates the processing of the dosage form with reduced problems of reagglomeration. Further, the use of a combination of coarse and fine particles reduces the problem of drug loss and improves the homogeneity of the drug particles. The present process also provides a dosage form with almost total drug release within 60 to 90 minutes.

Recognizing the above problems, the inventors have developed processes for preparing modafinil oral dosage forms in which about 7% to 25% by weight of the modafinil particles have diameters greater than 220 µm and about 75% to 93% by weight of the modafinil particles have diameters less than 220 µm. Additionally, the dosage form made by these processes release at least 75% of the drug in about 45 minutes.

As used herein the term "coarse" means modafinil particles having diameters greater than 220 µm and the term "fine" means modafinil particles having diameters less than 220 µm. A particularly suitable mean particle size of fines is that of diameters less than 180 µm. An even more suitable mean particle size of fines is that of diameters less than 60 µm. The ratio of coarse and fine particles may vary from about 7:93 to 25:75 by weight. Variations within this range generally do not affect the dissolution profile of this modafinil dosage form. Preferably, the specific surface area of the combined coarse and fine modafinil particles is at least 0.2 $m^2/gm$. The particle sizes are determined using, for example, a Malvern Master Sizer or by sieve analysis.

The term 'pharmaceutical composition' as used herein includes solid dosage forms such as tablet, capsule, pill and the like. These dosage forms may be prepared by processes known in the art including, for example, comminuting, mixing, granulating, melting, sizing, filling, drying, molding, immersing, coating, compressing, etc.

The desired modafinil particle size may be obtained by conventional methods, such as milling and sieving. Methods of comminuting the modafinil particles may include air jet milling, multi-milling, ball milling or any other method of particle reduction.

In one of the embodiments, the pharmaceutical composition of modafinil is prepared by a wet granulation process that includes the steps of blending coarse and fine modafinil particles with one or more intragranular pharmaceutically inert excipients to form a blend; wet granulating the blend with a granulating fluid or solution/dispersion of one or more pharmaceutically inert excipients in the granulating fluid to form granules; drying and sizing the granules; optionally blending the dried and sized granules with one or more pharmaceutically inert extragranular excipients; and compressing that blend into tablets or filling that blend into capsules. The pharmaceutical composition may optionally be coated with or more functional and/or non-functional coatings.

In another embodiment, the pharmaceutical composition of modafinil is prepared by a dry granulation process that includes the steps of blending coarse and fine modafinil particles with one or more intragranular pharmaceutically inert excipients to form a blend; dry granulating the blend by roller compactor or slugging to form granules; sizing the granules; optionally blending the sized granules with one or more pharmaceutically inert extragranular excipients to form a blend; and compressing that blend into tablets or filling that blend into capsules. The pharmaceutical composition may optionally be coated with or more functional and/or non-functional coatings.

In yet another embodiment, the pharmaceutical composition of modafinil is prepared by a direct compression process that includes the steps of blending coarse and fine modafinil particles with one or more pharmaceutically inert excipients to form a blend and then compressing the blend into tablets or filling the blend into capsules. The pharmaceutical composition may optionally be coated with or more functional and/or non-functional coatings.

The pharmaceutical composition also may be prepared by mixing the coarse and the fine modafinil particles in geometric progression with filler(s) and disintegrant(s); wet granulating the blend with an aqueous solution of binder; drying and sizing the granules; and compressing the granules into a tablet.

Mixing solid ingredients in a geometric progression generally refers to a process of adding almost equal amounts of two ingredients and then mixing to form a homogenous mixture of the two. This process is repeated by further mixing equal amounts to the mixture until the entire first ingredient is consumed. The entire mixture then is divided into, for example, four equal proportions and small amounts are taken from each portion and mixed thoroughly. This mixing is continued by adding from each portion until all the portions are completely used. The mixture then is further divided into two portions and the above process is repeated and ultimately the entire mixture is mixed randomly.

The term "pharmaceutically acceptable inert excipients" as used herein includes all excipients used in the art of manufacturing solid dosage forms. Examples include binders, diluents, disintegrants, surfactants, lubricants/glidants, coloring agents, and the like.

Specific examples of suitable binders include sugars, methyl cellulose, hydroxypropyl cellulose, hydroxypropyl methylcellulose, povidone, gelatin, gum arabic, ethyl cellulose, polyvinyl alcohol, pullulan, pregelatinized starch, agar, tragacanth, sodium alginate, propylene glycol, and the like.

Specific examples of suitable diluents include calcium carbonate, calcium phosphate-dibasic, calcium phosphate-tribasic, calcium sulfate, microcrystalline cellulose, powdered cellulose, dextrates, dextrins, dextrose excipients, fructose, kaolin, lactitol, lactose, mannitol, sorbitol, starch, starch pregelatinized, sucrose, sugar compressible, sugar confectioners, and the like.

Specific examples of suitable disintegrants include croscarmellose sodium, crospovidone and sodium starch glycolate and the like.

Specific examples of suitable surfactants include both non-ionic and ionic (cationic, anionic and zwitterionic) surfactants suitable for use in pharmaceutical dosage forms. These include polyethoxylated fatty acids and their derivatives, for example, polyethylene glycol 400 distearate, polyethylene glycol-20 dioleate, polyethylene glycol 4–150 mono dilaurate, polyethylene glycol-20 glyceryl stearate; alcohol-oil transesterification products, for example, polyethylene glycol-6 corn oil; polyglycerized fatty acids, for example, polyglyceryl-6 pentaoleate; propylene glycol fatty acid esters, for example, propylene glycol monocaprylate; mono and diglycerides, for example, glyceryl ricinoleate; sterol and sterol derivatives; sorbitan fatty acid esters and their derivatives, for example, polyethylene glycol-20 sorbitan monooleate, sorbitan monolaurate; polyethylene glycol alkyl ether or phenols, for example, polyethylene glycol-20 cetyl ether, polyethylene glycol-10-100 nonyl phenol; sugar esters, for example, sucrose monopalmitate; polyoxyethylene-polyoxypropylene block copolymers known as "poloxamer"; ionic surfactants, for example, sodium caproate, sodium glycocholate, soy lecithin, sodium stearyl fumarate, propylene glycol alginate, octyl sulfosuccinate disodium, palmitoyl carnitine; and the like.

Specific examples of suitable lubricants/glidants include colloidal silicon dioxide, aerosol, stearic acid, magnesium stearate, magnesium silicate, hydrogenated vegetable oils, sodium stearyl fumarate, calcium stearate, polyethylene glycol, sodium lauryl sulphate, sodium benzoate, talc, hydrogenated castor oil, sucrose esters of fatty acid, microcrystalline wax, yellow beeswax, white beeswax, and the like.

Coloring agents include any FDA colors approved for oral use.

Specific examples of suitable granulating fluids employed in the above preparations of pharmaceutical compositions include methylene chloride, isopropyl alcohol, acetone, methanol, ethanol, water, and the like.

The following examples further exemplify the invention and are not intended to limit the scope of the invention.

TABLE 1

Formulation details for Modafinil Tablets

| INGREDIENT | Example #1 (mg/tablet) | Example #2 (mg/tablet) | Example #3 (mg/tablet) |
|---|---|---|---|
| Intragranular Portion | | | |
| Modafinil (greater than 220 μm) | 30 | 30 | 20 |
| Modafinil (less than 220 μm) | 170 ($d_{90}$ 41; $d_{50}$ 21)* | 170 ($d_{90}$ 23; $d_{50}$ 12)* | 180 ($d_{90}$ 23; $d_{50}$ 12)* |
| Lactose | 132 | 132 | 132 |
| Starch | 125 | 125 | 125 |
| Croscarmellose Sodium | 10 | 10 | 10 |
| Povidone | 10 | 10 | 10 |
| Purified water | q.s. | q.s. | q.s. |
| Extragranular Portion | | | |
| Croscarmellose sodium | 10 | 10 | 10 |
| Colloidal silicon dioxide | 5 | 5 | 5 |
| Talc | 5 | 5 | 5 |
| Magnesium stearate | 2.5 | 2.5 | 2.5 |

*$d_x$ y μm denotes x % of particles with diameter less than y μm

Procedure for producing tablets of modafinil:

1. The modafinil particles were mixed in geometric progression with starch, lactose and intragranular croscarmellose sodium to form a blend.
2. A water solution of povidone was prepared and used for granulating the above blend to form granules.
3. The granules were dried at 60° C.; sized; and mixed with extragranular croscarmellose sodium, colloidal silicon dioxide, talc, and magnesium stearate.
4. The mixture of granules and extragranular ingredients then were compressed into tablets.

As described below, between 89% and 98% of the drug was released in 60–90 minutes at 50 rpm using dissolution test apparatus USP II and water as the media wherein the drug has low solubility. The dissolution profiles of modafinil tablets prepared as per Examples 1–3 are given in Table 2.

TABLE 2

Dissolution data using USP Apparatus II, 900 ml, 50 rpm, water (values are indicated in cumulative percent release)

| Time | Example #1 (%) | Example #2 (%) | Example #3 (%) |
|---|---|---|---|
| 15 min | 81 | 75 | 48 |
| 30 min | 87 | 86 | 68 |
| 45 min | 90 | 95 | 76 |
| 60 min | 91 | 97 | 84 |
| 90 min | 91 | 98 | 89 |

The dissolution data of Examples 1–3 demonstrates an ability and method to make a dosage form of modafinil in which the dissolution of the modafinil particles can be modified by varying the above ingredients to select a desired dissolution profile in which a great majority of the modafinil particles are released within 60–90 minutes. For example, if there is a desire to provide a large initial release of the modafinil, e.g., within fifteen minutes, the formulations of Examples 1 and 2 are most suitable. If there is a desire to provide less of an initial release of the modafinil, the formulation of Example 3 is most suitable. As can be seen from the data in Table 2, the dissolution profile can be modified by varying the relative amounts of coarse and fine modafinil particles, as well as by varying the size distribution of the fine particles.

While several particular forms of the inventions have been described, it will be apparent that various modifications and combinations of the inventions detailed in the text can be made without departing from the spirit and scope of the inventions. For example, the oral dosage form of modafinil can be provided with labeling for one or more of wakefulness promotion, to improve wakefulness in patients with excessive daytime sleepiness associated with narcolepsy, and idiopathic hypersomnia. Further, it is contemplated that any single feature or any combination of optional features of the inventive variations described herein may be specifically excluded from the claimed inventions and be so described as a negative limitation. Accordingly, it is not intended that the inventions be limited, except as by the appended claims.

We claim:

1. An oral dosage form comprising:
   about 7% to 25% by weight of modafinil particles having diameters greater than 220 μm;
   about 93% to 75% by weight of modafinil particles having diameters less than 220 μm,
   wherein about 90% of the particles having diameters size less than 220 μm are further characterized in that they have diameters less than about 41 μm, and about 50% of the particles having diameters size less tan 220 μm are further characterized in that they have diameters less than about 21 μm.

2. The oral dosage from according to claim 1 wherein about 7% by weight of the modafinil particles have diameters greater than 220 μm and about 93% by weight of the modafinil particles have diameters less than 220 μm.

3. The oral dosage form according to claim 1 wherein about 10% by weight of the modafinil particles have diameters greater than 220 μm and about 90% by weight of the modafinil particles have diameters less than 220 μm.

4. The oral dosage form according to claim 1 wherein about 15% by weight of the modafinil particles have diameters greater than 220 μm and about 85% by weight of the modafinil particles have diameters less than 220 μm.

5. The oral dosage form according to claim 1 wherein the specific surface area of the modafinil particles is at least 0.2 $m^2$/gm.

6. The oral dosage form according to claim 1 wherein the dosage form releases at least 75% of the modafinil in about 45 minutes.

7. The oral dosage form according to claim 1 wherein the dosage form comprises a tablet or capsule.

8. The oral dosage form according to claim 1 further comprising one or more pharmaceutically acceptable excipients.

9. The oral dosage form according to claim 8 wherein the one or more pharmaceutically acceptable excipients comprises one or more of binders, diluents, disintegrants, surfactants, lubricants, glidants, and coloring agents.

10. An oral dosage form of modafinil comprising an intragranular and an extragranular portion:
    the intragranular portion comprising about 7% to 25% by weight of modafinil particles having diameters greater than 220 μm, about 93% to 75% by weight of modafinil particles having diameters less than 220 μm, wherein about 90% of the particles having diameters size less than 220 μm are further characterized in that they have diameters less than about 41 μm, and about 50% of the particles having diameters size less than 220 μm are further characterized in that they have diameters less than about 21 μm, and
    one or more pharmaceutically acceptable excipients; and
    an extragranular portion comprising one or more pharmaceutically acceptable excipients.

11. The oral dosage form according to claim 10 wherein the oral dosage form releases one or more of between 48% and 81% of the modafinil within 15 minutes, between 68% and 87% of the modafinil within 30 minutes, between 76% and 95% of the modafinil within 45 minutes, between 84% and 97% of the modafinil within 60 minutes, and between 89% and 98% of the modafinil within 90 minutes.

12. The oral dosage form according to claim 11 wherein the modafinil is released in a USP Apparatus II, in 900 ml of water, and stirred at 50 rpm.

13. The oral dosage form according to claim 10 wherein the oral dosage form is provided with labeling for one or more of wakefulness promotion, to improve wakefulness in patients with excessive daytime sleepiness associated with narcolepsy, and idiopathic hypersomnia.

* * * * *